United States Patent [19]

Yamagata et al.

[11] Patent Number: 5,147,517
[45] Date of Patent: Sep. 15, 1992

[54] METHOD OF CAPILLARY ELECTROPHORESIS

[75] Inventors: Koichi Yamagata, Osaka; Yoshinari Shirasaki, Otsu, both of Japan

[73] Assignee: Shimadzu Corporation, Kyoto, Japan

[21] Appl. No.: 676,301

[22] Filed: Mar. 28, 1991

[51] Int. Cl.$^5$ .................... B01D 57/02; B01D 61/42; C25B 1/00
[52] U.S. Cl. ............................ 204/180.1; 204/182.8
[58] Field of Search ............. 204/299 R, 180.1, 182.8

[56] References Cited

FOREIGN PATENT DOCUMENTS 3-113357  5/1991  Japan .
3-113358  5/1991  Japan .

OTHER PUBLICATIONS

Electrophoresis on uncrosslinked polyacrylamide: Molecular Sieving and its potential applications, Hjerten, Electrophoresis (1986), 7; 217–220.
Electrophoresis of Proteins & Nucleic Acids on Acrylamide–Agarose Gels Lacking Covalent Cross-linking, Anal. Biochem. 143 (1984) 333–330.
The Use of Liquid Polyacrylamide in Electrophoresis, Hans-Joachim Bode, Zoologiches Institut der Univeritat Heidelberg, 6900 Heidelberg.
Patent Abstracts of Japan, vol. 9, No. 304 (P-409) (2027) Nov. 30, 1985 JP 60-138447 Jul. 23, 1985.
*Journal of Chromatography*, vol. 480, Oct. 20, 1989, pp. 311–319.
*Journal of Chromatography*, vol. 347, No. 2, Nov. 1, 1985, pp. 191–198.
*Proceedings of the National Academy of Sciences of USA*, vol. 85, No. 24, Dec. 1988, pp. 9660–9663.
Chemical Abstracts, vol. 115, No. 9, Sep. 2, 1991, 115:88815w.
Chemical Abstracts, vol. 115, No. 9, Sep. 2, 1991, 115:88816x.
Analytical Abstracts Database, Access. No. 53-1-0-B-00029; J. Liq. Chromatogr. vol. 13, No. 8, 1529–1558, 1990.
Analytical Abstracts Database, Access No. 50-0-1-D-00263; Analyt. Biochem., vol. 164, No. 1, 236–239, 1987.
Cohen et al, Journal of Chromatography, vol. 458, pp. 323–333 (1988).
Kasper et al, Journal of Chromatography, vol. 458, pp. 303–312 (1988).
Cohen et al, Proc. Natl. Acad. Sci. USA, vol. 85, pp. 9660–9663 (1988).

*Primary Examiner*—John Niebling
*Assistant Examiner*—Caroline Koestner
*Attorney, Agent, or Firm*—Birch, Stewart, Kolasch & Birch

[57] ABSTRACT

The method of capillary electrophoresis of the present invention is carried out using an electrophoretic buffer containing an ungelled agarose polymer, wherein the agarose polymer concentration may be constant or may be changed on a time basis.

The method of the present invention permits efficient fractional assay with high reproductibility. Particularly, the mode using the apparatus of the present invention in which the agarose polymer concentration is changed on a time basis is suitable for fractional assay of DNA and proteins of a wide range of size because an electrophoretic buffer having an ideal composition for separation is supplied constantly.

7 Claims, 3 Drawing Sheets

METHOD OF CAPILLARY ELECTROPHORESIS

BACKGROUND OF THE INVENTION

1. Field of the Invention

The present invention relates to a method of fractional assay of nucleic acids, proteins and other substances, more specifically to a method of capillary electrophoresis suitable for separation of their components close to each other in properties and to an apparatus therefor.

2. Description of the Prior Art

Traditionally, agarose electrophoresis, polyacrylamide gel electrophoresis and other methods have been widely used for fractional assay of nucleic acids, proteins and other substances. However, these methods are disadvantageous to system automation because the gel used therefor is not reusable and requires much time for preparation.

In recent years, attempts have been made to apply capillary electrophoresis to fractional assay of nucleic acids, proteins and other substances. Particularly, its application to fractional assay of nucleic acids has been reported by B. L. Karger et al. and R. G. Brownlee et al.

As a method of carrier-free capillary electrophoresis, Karger et al. used a fused silica capillary and borate-buffered tris(hydroxymethyl)aminomethane containing 7M urea and 0.1% sodium dodecyl sulfate as the electrophoretic buffer to separate a mixture of DNA fragments digested by restriction enzyme [Journal of Chromatography, 458 (1988), pp. 323-333]. Brownlee et al. used a fused silica capillary and an NaH2P04-Na2B407 buffer containing 4M urea and 20 mM cetyltrimethylammonium bromide to separate a mixture of DNA fragments digested by restriction enzyme [Journal of Chromatography, 458 (1988), pp. 303-312]. In both cases, however, the DNA separation mechanism remains unknown. In addition, the former method is faulty in that a peak of unknown origin may appear, and separation becomes difficult to reproduce due to minor differences in sample pretreatment and injection conditions. The latter method does not offer satisfactory separation.

As a method of capillary electrophoresis using gel as the matrix packed in the capillary, Brownlee et al. used a capillary packed with polyacrylamide gel containing 3% T and 5% C to separate a mixture of DNA fragments digested by restriction enzyme [Journal of Chromatography, 458 (1988), pp. 303-312]. Similarly, Karger et al. separated a mixture of d(A)40-60 oligonucleotides [Pro. Natl. Acad. Sci. USA, 85 (1988), pp. 9660-9663]. However, capillary electrophoresis using polyacrylamide gel does not offer high reproducibility of the formation of polyacrylamide gel in the capillary because of the small inside diameter of the capillary, and the mixture separation reproducibility is also poor. Another method of capillary electrophoresis using gel as the matrix uses agarose gel [Brownlee et al., Journal of Chromatography, 458 (1988), pp. 303-312], but agarose gel is mechanically fragile and flows out during electrophoresis. Moreover, the gel melts and flows out from the capillary because of temperature rise due to heat generation during electrophoresis. For these reasons, when a capillary packed with agarose gel is used for electrophoresis, it is not possible to achieve mixture separation with high reproducibility.

As stated above, in fractional assay of nucleic acids, proteins and other substances, agarose electrophoresis and polyacrylamide gel electrophoresis pose problems of much time requirement for gel preparation and difficulty in automation. Also, when used for fractional assay of nucleic acids and other substances, capillary electrophoresis poses a problem of unsatisfactory separation with poor reproducibility, whether or not it uses gel as the matrix.

SUMMARY OF THE INVENTION

It is an object of the present invention to provide a method of capillary electrophoresis using an electrophoretic buffer containing an ungelled agarose polymer as a replacement for agarose electrophoresis or polyacrylamide gel electrophoresis, or another method of capillary electrophoresis wherein the agarose polymer concentration in the buffer is changed on a time basis, and to carry out fractional assay of DNA and proteins of an especially wide range of size continuously without gel preparation upon each run and with high reproducibility.

It is another object of the present invention to provide an apparatus for the method of capillary electrophoresis described above.

With the aim of solving the problems described above, the present inventors made extensive investigations and developed the present invention. Accordingly, the gist of the present invention relates to a method of capillary electrophoresis wherein capillary electrophoresis is carried out using an electrophoretic buffer containing an ungelled agarose polymer whose concentration is kept constant or changed on a time basis in the absence of an agarose gel or polyacrylamide gel in the capillary, and to an apparatus therefor.

Figure 1:
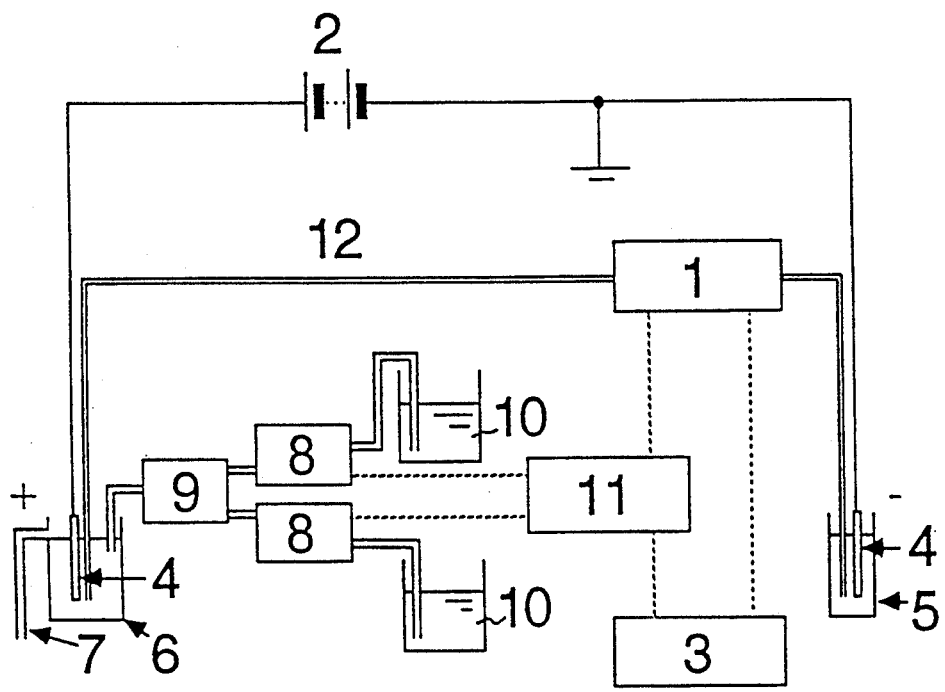
FIG. 1 shows the apparatus configuration for the embodiment of the method of the present invention wherein the agarose polymer concentration is changed on a time basis.

In these figures, the numeric symbols represent the following: 1 ... fluorescence detector, 2 ... high voltage power supply, 3 ... recorder, 4 ... electrode, 5 ... cathode chamber, 6 ... anode chamber, 7 ... drain, 8 ... pump, 9 ... mixing block, 10 ... buffer reservoir, 11 ... pump controller, 12 ... capillary.

DETAILED DESCRIPTION OF THE INVENTION

In the present invention, there is no limitation on the choice of the sample for capillary electrophoresis, but solutions containing high molecular weight substances such as nucleic acids or proteins are most suitable to fractional assay.

In the present invention, the electrophoretic buffer is used after adding an agarose polymer thereto. This agarose polymer is preferably so-called low melting point agarose, which has a low gelling temperature, but any agarose polymer can be used, as long as it does not gel upon use. The method of capillary electrophoresis of the present invention is carried out using an electrophoretic buffer containing such an ungelled agarose polymer, wherein the agarose polymer concentration may be constant or may be changed on a time basis. Although any of these two modes is possible for the method of the present invention, the mode in which the concentration is changed on a time basis is preferred for separation of especially DNA of a wide range of size.

When the method of the present invention is carried out at constant agarose polymer concentration, the concentration is normally about 0.01 to 3%, preferably about 0.01 to 0.5%. When the concentration is changed on a time basis, it is the common practice to start at 0% and increase the concentration up to about 3%, preferably about 0.5%.

It is preferable to add a surfactant such as SDS (sodium dodecyl sulfate) at 0.01 to 0.5% to the electrophoretic buffer for the present invention, but the surfactant may not be added.

The electrophoretic buffer for the present invention contains a buffering agent such as 0.1M tris(hydroxymethyl)aminomethane or boric acid, but various buffering agents can be used according to the sample to be fractionally assayed.

The apparatus for the method of capillary electrophoresis of the present invention may be a known ordinary capillary electrophoretic apparatus when the agarose polymer is used at constant concentration. On the other hand, when the agarose polymer concentration is changed on a time basis, the apparatus comprises a capillary, an anode chamber, a cathode chamber, respectively in which electrode chambers both ends of the capillary are immersed, a buffer feeder to adjust the electrophoretic buffer component concentration in the electrode chambers, a detector attached to the capillary, a recorder to record the detection data from the detector, a controller to control the buffer feeder, and a power supply to apply voltage to the two electrode chambers described above.

The capillary for the present invention is preferably made of fused silica, but this material is not to be construed as limitative.

The inside diameter of the capillary is preferably 10 to 200 μm, but this range is not to be construed as limitative.

The power supply preferably provides a maximum output voltage of about 30 kV, but the maximum output voltage may be greater or smaller than 30 kV. Also, the electric current is preferably a direct current, but it may be pulsatile, and these are not to be construed as limitative.

The detector is preferably a UV detector or a fluorescence detector, for instance, but it may be an electrochemical detector or the like, and these are not to be construed as limitative.

The recorder preferably has data processing functions such as calculation of retention time, peak height and peak area, but this feature is not to be construed as limitative.

The buffer feeder is an apparatus to make adjustments so that the component concentration in the electrophoretic buffer changes on a time basis. It is configured with buffer reservoirs, pumps and a mixing block so that the buffers stored in the buffer reservoirs are mixed and injected into the electrode chamber by the pumps controlled by the controller. Accordingly, two kinds of reservoir are used: one for an electrophoretic buffer containing an agarose polymer which does not gel upon use such as low melting point agarose and the other for an electrophoretic buffer containing no such agarose polymer. The buffer feeder is adjusted so that these two kinds of buffer are supplied to the mixing block by the pumps controlled by the controller and the agarose polymer concentration in the buffer changes on a time basis.

The controller controls the pumps of the buffer feeder, and is preferably capable of controlling a plurality of pumps.

When using the apparatus for capillary electrophoresis of the present invention, the sample is injected into the capillary filled with the electrophoretic buffer described above via the inlet end thereof, and the both ends of the capillary are immersed in respective electrode chambers containing an electrophoretic buffer. A platinum electrode is immersed in each of these two electrode chambers, and a voltage is applied to both electrodes. By applying the voltage to both ends of the capillary, a flow of electrophoretic buffer is produced in the capillary, and the eluted sample components are detected by the detector described above. The electric signal from the detector is transmitted to the recorder and processed therein. Also, the composition of the electrophoretic buffer in the electrode chamber is changed on a time basis by the pumps controlled by the controller during electrophoresis.

The method of the present invention permits efficient fractional assay with high reproducibility because an electrophoretic buffer containing an agarose polymer is constantly supplied into the capillary. Particularly, the mode in which the agarose polymer concentration is changed on a time basis is suitable for fractional assay of DNA and proteins of a wide range of size because an electrophoretic buffer having an ideal composition for separation is supplied constantly. The present invention also permits continuous assay free of washing, capillary gel exchange and other procedures because the entire amount of the sample introduced from the inlet end of the capillary is washed down by the electrophoretic buffer containing an agarose polymer.

EXAMPLES

The present invention is hereinafter described in more detail by means of the following examples, but these are not to be construed as limitative.

EXAMPLE 1

Fractional Assay of a Mixture of DNA Fragments Digested by Restriction Enzyme (1) Preparation of an Electrophoretic Buffer Containing Low Melting Point Agarose To 80 ml of distilled water 0.5 g of low melting point agarose was added. After vigorous stirring, this mixture was heated until the agarose dissolved, and it was cooled at room temperature. Then, 1.21 g of tris(hydroxymethyl)aminomethane, 93 mg of disodium ethylenediaminetetraacetate and 20 mg of sodium dodecyl sulfate were dissolved therein. To this solution boric acid was added to adjust the pH to 8.1, and distilled water was added to make exactly 100 ml.

(2) Preparation of an Electrophoretic Buffer Not Containing Low Melting Point Agarose In 90 ml of distilled water 1.21 g of tris(hydroxymethyl)aminomethane, 93 mg of disodium ethylenediaminetetraacetate and 20 mg of sodium dodecyl sulfate were dissolved. To this solution boric acid was added to adjust the pH to 8.1, and distilled water was added to make exactly 100 ml.

(3) Capillary Electrophoresis of the Mixture of DNA Fragments Digested by Restriction Enzyme Capillary electrophoresis was performed using the system illustrated in FIG. 1. Specifically, the fluorescent detector 1 was the RF-540 model (product of Shimadzu Corporation, set at an excitation wavelength of 300 nm and an emission wavelength of 590 nm), the high voltage power supply 2 was the HER-30P0. 16-SI model (product of Matsusada Precision Devices), the recorder 3 was the C-R4A model (product of Shimadzu Corporation), the electrode 4 was a platinum wire (0.5 mm dia.×30 mm), the pump 8 was the LC-6A model (product of Shimadzu Corporation) and the controller 11 was the SCL-6A model (product of Shimadzu Corporation).

The capillary 12 was the fused silica capillary of 75 μm in inside diameter produced by Scientific Glass Engineering Company. The capillary had a total length of 450 mm and was attached to the fluorescence detector with its coating removed in a width of 2 mm at 300 mm apart from the anode side. This capillary was filled with the electrophoretic buffer described above upon use, and its both ends were kept immersed respectively in the anode chamber 6 and cathode chamber 5, each of which electrode chambers contained an electrophoretic buffer. The buffer levels in the two electrode chambers were adjusted so that they were the same as each other.

The sample mixture of DNA fragments digested by restriction enzyme was prepared by mixing two commercial products [marker 5, product of Nippon Gene Company, (174/HincII digest 79-1057 base pairs, 0.5 μg/ml) and marker 1, product of Nippon Gene Company (HindIII digest 0.13-23.13 k base pairs, 0.5 μg/ml)]. Sample injection into the capillary was achieved by raising up the anode end of the capillary from the anode chamber and immersing it in the sample solution for 10 seconds. The sample solution level was adjusted so that it was located 50 mm above the buffer level in the electrode chamber.

Figure 2:
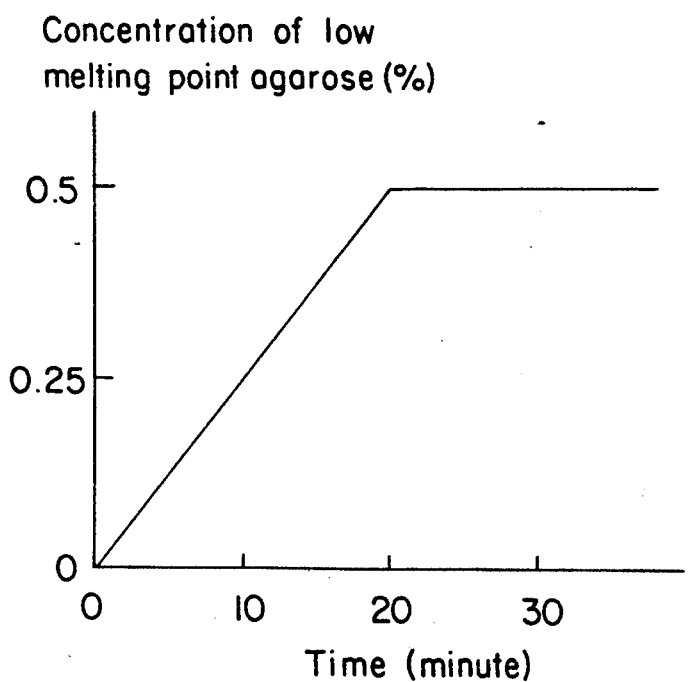
FIG. 2 shows time-based changes in the low melting point agarose concentration in the buffer in Example 1.

After sample introduction into the capillary, the end of the capillary was returned into the electrode chamber, and a direct current voltage of 7.5 kV was applied to both ends of the capillary, and the pumps were controlled so that the low melting point agarose concentration in the anode chamber became as shown in FIG. 2. The electric current had a value of 12 to 15 μA, and a buffer flow was produced from the anode side to the cathode side in the capillary. The sample DNA fragments digested by restriction enzyme were separated from each other, eluted and detected by the fluorescent detector.

Figure 3:
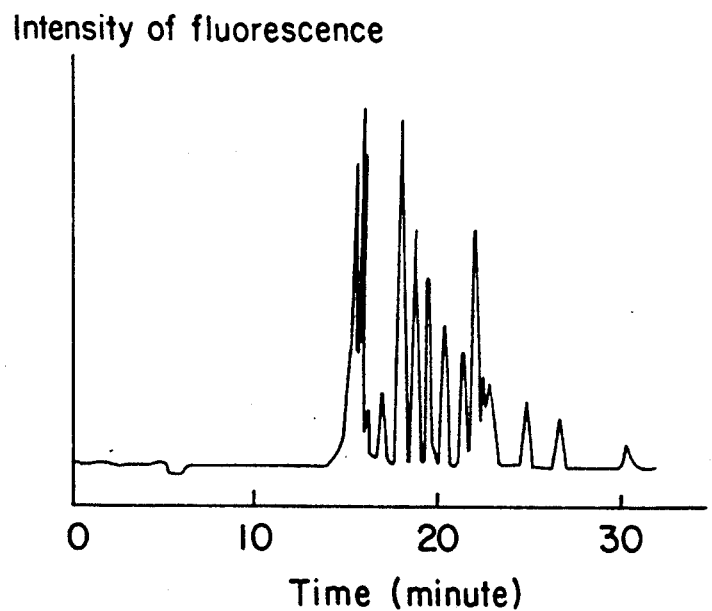
FIG. 3 shows the data obtained by separation and detection in Example 1.

The result is shown in FIG. 3. It is evident from this result that the DNA fragments of a wide range of size in the mixture digested by restriction enzyme were well separated and detected by the method of the present invention.

EXAMPLE 2

Capillary Electrophoresis of a Mixture of φ×174 Phage DNA Fragments Digested by Restriction Enzyme (HincII)

Capillary electrophoresis was carried out using the same system as in Example 1 except that it had neither the buffer feeder nor the controller. This capillary was filled with the electrophoretic buffer containing low melting point agarose prepared in Example 1 upon use, and its both ends were kept immersed respectively in the anode chamber and cathode chamber, each of which electrode chambers contained low melting point agarose. The buffer levels in the two electrode chambers were adjusted so that they were the same as each other.

The sample mixture of φ×174 phage DNA fragments digested by restriction enzyme (HincII) was a commercial product [marker 5, product of Nippon Gene Company, (φ×174/HincII digest 79-1057 base pairs, 0.5 μg/ml)], which was used as such. Sample injection into the capillary was achieved by raising up the anode end of the capillary from the anode chamber and immersing it in the sample solution for 10 seconds. The sample solution level was adjusted so that it was located 50 mm above the buffer level in the electrode chamber.

After sample introduction into the capillary, the end of the capillary was returned into the electrode chamber, and a direct current voltage of 7.5 kV was applied to both ends of the capillary. The electric current had a value of 12 to 15 μA, and a buffer flow was produced from the anode side to the cathode side in the capillary. The sample DNA fragments digested by restriction enzyme were separated from each other, eluted and detected by the fluorescent detector.

Figure 4:
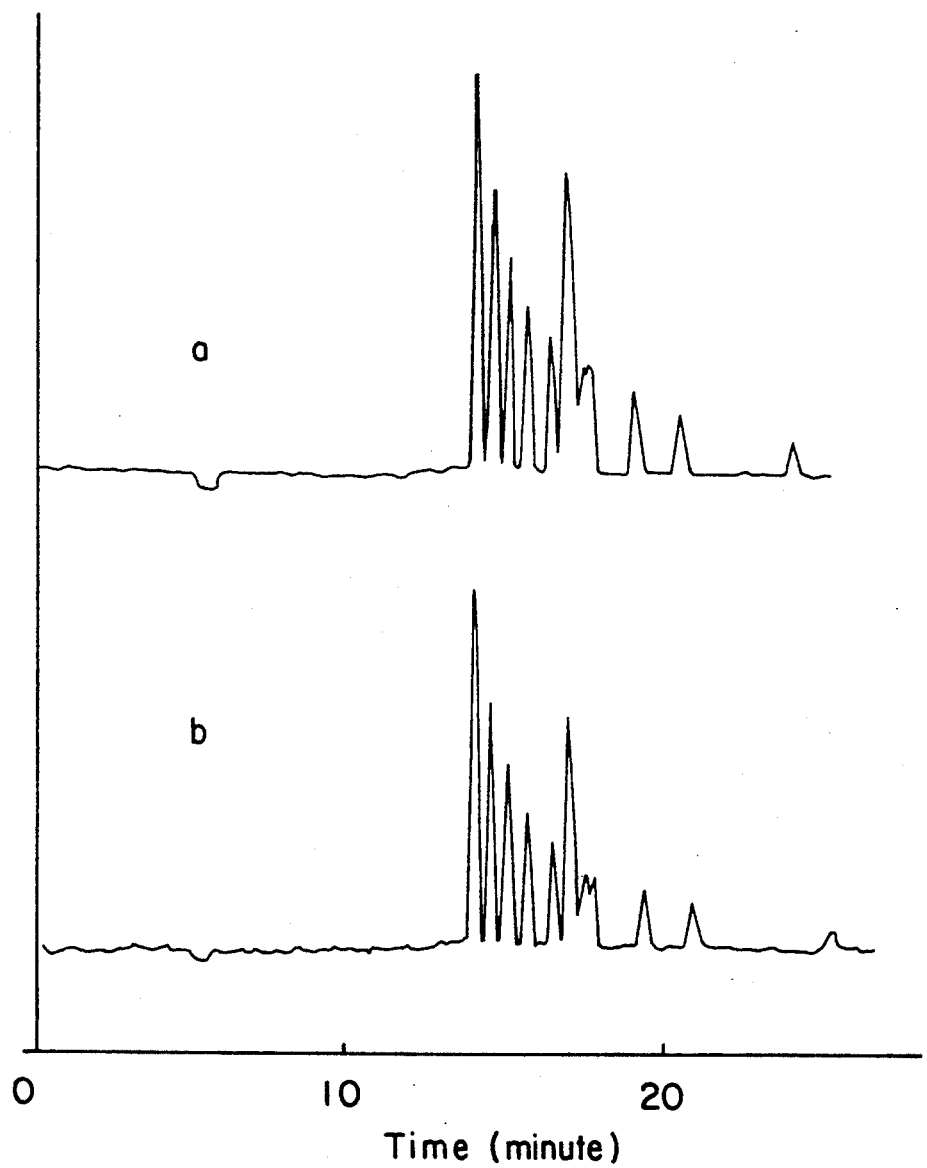
FIG. 4 shows the data obtained by separation and detection in Example 2.

The result is shown in Panel a of FIG. 4. It is evident from this result that the φ×174 phage DNA fragments of a wide range of size in the mixture digested by restriction enzyme were well separated and detected by the method of the present invention.

Subsequently, the same procedure was followed to carry out capillary electrophoresis of a mixture of φ×174 phage DNA fragments digested by restriction enzyme (HincII) at intervals of 30 minutes in a total of 10 times. The result obtained in the 10th run is shown in Panel b of FIG. 4.

It is evident from this result that the DNA fragments digested by restriction enzyme in the mixture were separated and detected with high reproducibility with no capillary deterioration.

What is claimed is:

1. A method of capillary electrophoresis which comprises subjecting a sample mixture of substances to be separated to capillary electrophoresis, wherein the electrophoretic buffer contains an ungelled agarose polymer, whereby the substances in the sample are separated from each other.

2. A method according to claim 1, wherein the concentration of said ungelled agarose polymer is changed on a time basis.

3. A method according to claim 2, wherein the ungelled agarose polymer concentration is changed from 0% to about 3% on a time basis.

4. A method according to claim 1, wherein the ungelled agarose polymer is a low melting point agarose.

5. A method according to claim 1, wherein the ungelled agarose polymer is used in a concentration of 0.01 to 3%.

6. A method according to claim 1, wherein the sample is a mixture of DNA fragments, digested by restriction enzyme.

7. A method according to claim 1, wherein the capillary electrophoresis is conducted in capillary tubes having an inside diameter of from 10 to 300 μm.

* * * * *